US009410876B2

(12) United States Patent
Dryer et al.

(10) Patent No.: US 9,410,876 B2
(45) Date of Patent: Aug. 9, 2016

(54) SYSTEM AND METHOD FOR THE DETERMINATION OF MIXTURE AVERAGED MOLECULAR WEIGHT OF COMPLEX MIXTURES

(71) Applicants: Frederick L. Dryer, Pennington, NJ (US); Sang Hee Won, Monmouth Junction, NJ (US); Stephen Dooley, Letterkenny (IE)

(72) Inventors: Frederick L. Dryer, Pennington, NJ (US); Sang Hee Won, Monmouth Junction, NJ (US); Stephen Dooley, Letterkenny (IE)

(73) Assignee: The Trustees of Princeton University, Princeton, NJ (US)

( * ) Notice: Subject to any disclaimer, the term of this patent is extended or adjusted under 35 U.S.C. 154(b) by 311 days.

(21) Appl. No.: 14/148,213

(22) Filed: Jan. 6, 2014

(65) Prior Publication Data
US 2014/0190244 A1    Jul. 10, 2014

Related U.S. Application Data

(60) Provisional application No. 61/748,792, filed on Jan. 4, 2013.

(51) Int. Cl.
*G01N 7/16* (2006.01)
*G01N 25/02* (2006.01)

(52) U.S. Cl.
CPC . *G01N 7/16* (2013.01); *G01N 25/02* (2013.01)

(58) Field of Classification Search
None
See application file for complete search history.

(56) References Cited

U.S. PATENT DOCUMENTS

| 3,527,085 | A  | * | 9/1970  | Hines ....................... G01N 7/14 73/29.03 |
| 4,466,054 | A  | * | 8/1984  | Shigemasa ......... G05B 13/0245 318/561 |
| 4,785,666 | A  | * | 11/1988 | Bergquist .............. G01M 3/202 62/55.5 |
| 6,528,018 | B1 | * | 3/2003  | Berndt ................. G01N 21/714 422/550 |
| 2003/0001086 | A1 | * | 1/2003 | Noerenberg ............. G01N 7/10 250/282 |
| 2009/0159715 | A1 | * | 6/2009 | Lessig ...................... F25B 9/04 236/47 |

OTHER PUBLICATIONS

Web Document: Smith Kelley M, Physical Chemistry Laboratory: Molecular Weight of a Vapor Final Report, Sep. 4, 2003.*
Espada, J.J., C. Almendros, and B. Coto, Evaluation of Different Methodologies to Determine the Molecular Weight of Petroleum Fractions. Energy and Fuels 25, 5076-5082, (2011).
(Continued)

*Primary Examiner* — Paul West
(74) *Attorney, Agent, or Firm* — Meagher Emanuel Laks Goldberg & Liao, LLP

(57) ABSTRACT

An apparatus and method for determining the average molecular weight of a complex mixture from a plurality of test samples of the complex mixture are disclosed. The method includes a) providing a chamber having two fixed conditions and one variable condition selected from three state variables of temperature, pressure and volume; b) introducing a test sample of known mass into the chamber; c) setting operating conditions of the state variables such that the test sample will be fully vaporized into a gaseous state without decomposition or chemical reaction; and d) measuring the change of the variable condition after full vaporization of the test sample is achieved. Steps b-d are repeated for several test samples having different masses. The average molecular weight of the complex mixture is determined as a linear gradient (slope) of the relationship for the change of variable condition as a function of test sample mass.

18 Claims, 7 Drawing Sheets

(56) References Cited

OTHER PUBLICATIONS

Schneider, D.F., Select the Right Hydrocarbon Molecular Weight Correlation. Stratus Engineering Inc., 2951 Marina Bay Drive, League City, TX 77573, (1998).

ASTM D2502. Standard Test Method for Estimation of Mean Relative Molecular Mass of Petroleum Oils from Viscosity Measurements. ASTM International, 100 Barr Harbor Drive, PO Box C700, West Conshohocken, PA 19428-2959, United States, 2009.

ASTM D2503. Standard Test Method for Relative Molecular Mass (Molecular Weight) of Hydrocarbons by Thermoelectric Measurement of Vapor Pressure. ASTM International, 100 Barr Harbor Drive, PO Box C700, West Conshohocken, PA 19428-2959, United States, 2007.

Dooley, S., et al., "A Jet Fuel Surrogate Formulated by Real Fuel Properties", Combust Flames, 157, 2010.

Dooley, S. et al., "The Experimental Evaluation of a Methodology for Surrogate Fuel Formulation to Emulate Gas Phase Combustion Kinetic Phenomena", Combust Flame, 159, 2012.

Dooley, S. et al., "The Combustion Kinetics of a Synthetic Paraffinic Jet Aviation Fuel and a Fundamentally Formulated, Experimentally Validated Surrogate Fuel", Combust Flame, 159, 2012.

ASTM D6890. Standard Test Method for Determination of Ignition Delay and Derived Cetane No. (DCN) of Diesel Fuels Oils by Combustion in a Constant Volume Chamber. ASTM International, 100 Barr Harbor Dr. PO Box C700, West Conshohocken, PA. US, 2013.

ASTM D5291. Standard Test Methods for Instrumental Determination of Carbon, Hydrogen, and Nitrogen in Petroleum Products and Lubricants. ASTM International, 100 Barr Harbor Dr. PO Box C700, West Conshohocken, PA, US, 2002.

Mensch, A., et al., "Sooting Characteristics of Surrogates for Jet Fuels", Combust Flame, 157, 2010.

ATSM D1322. Standard Test Method for Smoke Point of Kerosine and Aviation Turbine Fuel. ASTM International, 100 Barr Harbor Dr. PO Box C700, West Conshohocken, PA, US, 2012.

Won, S.H., et al., "A Radical Index for the Determination of the Chemical Kinetic Contribution to Diffusion Flame Extinction of Large Hydrocarbons Fuels", Combust Flame, 159, 2012.

European Commission Regulation (EU) No. 582/2011, Official Journal of the European Union Jun. 25, 2011, I. 167-1-167-167, (2011).

ASTM D7170. Standard Test Method for Determination of Derived Cetane No. (DCN) of Diesel Fuel Oils—Fixed Range Injection Period, Constant Volume Combustion Chamber Method. ASTM International, 100 Barr Harbor Dr. PO Box C700, West Conshohocken, PA, US, 2012.

\* cited by examiner

| Fuel Sample | | | n-dodecane | | | | | | | | |
|---|---|---|---|---|---|---|---|---|---|---|---|
| Molecular Weight [g/mol] | | | 170.3348 | | | | | | | | |
| Parameters | | | | | | | | | | | |
| average | Stdev | % error | R [J/K/mol] | | | | | | | | |
| 0.0006 | 0.002183 | 0.34082895 | 8.314 | | | | | | | | |

| Note | T [C] | T [K] | mass [g] | mass [mg] | P1 [psi] | P2 [psi] | P1 [Pa] | P2 [Pa] | ΔP [Pa] | ΔPV/RT [mol] | ΔPV/RT [mmol] |
|---|---|---|---|---|---|---|---|---|---|---|---|
| average | | | | | | | | | | | 0 |
| Test 1 | 150 | 423.15 | 0.0782 | 78.2 | 0.24 | 0.62 | 1654.74175 | 4274.74952 | 2620.00777 | 0.000476924 | 0.476923787 |
| Test 2 | 150 | 423.15 | 0.1089 | 108.9 | 0.16 | 0.68 | 1103.161166 | 4688.434957 | 3585.273791 | 0.000652633 | 0.652632551 |
| Test 3 | 150 | 423.15 | 0.1453 | 145.3 | 0.2 | 0.9 | 1378.951458 | 6205.281561 | 4826.330103 | 0.000878544 | 0.878543818 |
| Test 4 | 150 | 423.15 | 0.1785 | 178.5 | 0.14 | 0.94 | 965.2660206 | 6481.071853 | 5515.805832 | 0.00100405 | 1.004050078 |
| Test 5 | 150 | 423.15 | 0.2188 | 218.8 | 0.19 | 1.19 | 1310.003885 | 8204.761175 | 6894.75729 | 0.001255063 | 1.255062597 |
| Test 6 | 200 | 473.15 | 0.34 | 340 | 0.21 | 1.95 | 1447.899031 | 13444.77672 | 11996.87768 | 0.001953035 | 1.953035494 |
| Test 7 | 200 | 473.15 | 0.3745 | 374.5 | 0.23 | 2.17 | 1585.794177 | 14961.62332 | 13375.82914 | 0.002177522 | 2.177522333 |
| Outlier | 200 | 473.15 | 0.4966 | 496.6 | 0.17 | 2.58 | 1172.108739 | 17788.47381 | 16616.36507 | 0.002705066 | 2.705066403 |

Figure 4a

SYSTEM AND METHOD FOR THE DETERMINATION OF MIXTURE AVERAGED MOLECULAR WEIGHT OF COMPLEX MIXTURES

CROSS-REFERENCE TO PRIOR FILED APPLICATIONS

This application claims priority to U.S. provisional application No. 61/748,792 which was filed on Jan. 4, 2013 which is incorporated herein in its entirety.

GOVERNMENT RIGHTS IN THIS INVENTION

This invention was made with government support under Grant #FA9550-07-1-0515 awarded by the Air Force Office of Sponsored Research. The government has certain rights in this invention.

TECHNICAL FIELD

This invention relates generally to the determination of the mixture average molecular weight of complex mixtures of molecules that exist in the fully vaporized (gaseous) state at a specific temperature and volume, over a range of pressures or at a specific temperature, and pressure but a range of volumes, in either case, without decomposition or chemical interactions. In particular, the techniques disclosed herein are applicable to liquid transportation fuels including: hydrocarbon/oxygenated hydrocarbon mixtures used in ground transportation, aeropropulsion fuels, and liquid rocket propellants.

BACKGROUND

Currently, ASTM lists no single method that entirely encompasses the molecular weight range expected for gasolines, diesel fuels, and gas turbine fuels and/or that does not employ correlative relationships with other fuel properties to yield the average molecular weight. A number of methods for estimating average molecular weight are described in the literature. Each of the references listed in this disclosure are incorporated herein in their entirety.

For example, Espada, J. J., C. Almendros, and B. Coto, "Evaluation of Different Methodologies to Determine the Molecular Weight of Petroleum Fractions", Energy and Fuels 25, 5076-5082 (2011) discloses a method based upon gel permeation chromatography and distillation curve. Many of the previously disclosed methods rely on empirical correlations of more readily available fuel properties to deduce the mixture averaged molecular weight. See e.g., Nelson, "Petroleum Refinery Engineering," 4th ed., Mcgraw-Hill Book Company NY (1958); Schneider (1998), "Select the Right Hydrocarbon Molecular Weight Correlation", Stratus Engineering, Inc, League City, Tex. (http://www.stratusengr.com/). Other methods utilize property measurements such as vapor pressure ossmometry and freezing point suppression. Such methods are designed to leverage reliable scientific theories but are primarily limited by the ability to measure very small perturbations of the specific fluid property, for example electrical conductance or fluid temperature respectively. Consequently, the expected accuracy and associated uncertainty of the reported quantity are limited. For example, ASTM D2502 and ASTM 2503 quote best case values of 5 and 14 g/mol for repeatability and reproducibility respectively.

Other so called "direct" techniques such as those involving detailed gas chromatography (GC) and gas chromatographic-mass spectrometry (GC-MS) analyses present higher accuracy for analytes which are simple mixtures, but encounter difficulties when the fluid mixture is more complex, such as is the case for real gasolines, kerosenes and diesel fuels which are commonly each composed of hundreds of individual chemical components. Such chromatographic analyses typically require considerable investment in expert use of sophisticated and expensive analytical equipment, followed by complex and time consuming interpretation of the measurements to yield an average molecular weight. The uncertainty of these techniques depends in a cumulative manner on: the proper chromatographic separation of each of the unknown components, correct identification and accurate quantification of each of the hundreds of individual molecular species that may or may not be present. In addition, the presence of the many molecular classes and isomers in these materials complicate accurate quantification by analytic GC, GC-MS) and even comprehensive multi-dimensional (e.g. two-dimensional gas chromatography-mass spectrometry (GC×GC-MS) methods, resulting in both inaccuracies and uncertainties in the determined value. Regardless of the molecular complexity of the analyte, chromatographic-based techniques are not only time consuming, and expensive, but are difficult to automate when analytes are of varying compositional character. Improved systems and a more direct, simple method for determination of the mixture average molecular weight of complex transportation fuels is desirable.

SUMMARY OF THE INVENTION

An apparatus and method for determining the average molecular weight of a complex mixture from a plurality of test samples of the complex mixture are disclosed. The method includes a) providing a chamber having two fixed conditions and one variable condition selected from three state variables of temperature, pressure and volume; b) introducing a test sample of known mass into the chamber; c) setting operating conditions of the state variables such that the test sample will be fully vaporized into a gaseous state without decomposition or chemical reaction; and d) measuring the change of the variable condition after full vaporization of the test sample is achieved. Steps b-d are repeated for several test samples having different masses. The average molecular weight of the complex mixture is determined as a linear gradient (slope) of the relationship for the change of variable condition as a function of test sample mass.

The fixed conditions may be volume and temperature and the variable condition may be pressure. The fixed conditions may be temperature and pressure and the variable condition may be volume. The average molecular weight may be determined by performing a linear regression on the measured change of variable condition as a function of test sample mass. The linear regression may generate a line having a slope equal to the average molecular weight of the fuel under test. The fixed conditions may be held essentially constant. At least one of the fixed conditions may be controlled using a proportional-integral-derivative (PID) controller. The chamber may be vacuumed to a target pressure prior to introducing the test sample. The chamber may be purged with nitrogen prior to intruding the test sample. The target pressure may be approximately 1.4 kPa.

An apparatus configured to determine of the average molecular weight of a complex mixture from a plurality of test samples is also disclosed. The apparatus includes a chamber having two fixed conditions and one variable condition selected from three state variables of temperature, pressure and volume. At least one sensor is configured to measure the variable condition for the plurality of test samples. A controller is configured to determine the average molecular weight of the complex mixture as a linear gradient (slope) of the relationship for the change of variable condition as a function of test sample mass.

The fixed conditions may be volume and temperature and the variable condition may be pressure. The fixed conditions may be temperature and pressure and the variable condition may be volume. The average molecular weight may be determined by performing a linear regression on the measured change of variable condition as a function of test sample mass. The linear regression may generate a line having a slope equal to the molecular weight of the fuel under test. The fixed conditions may be held essentially constant. At least one of the fixed conditions may be controlled using a proportional-integral-derivative (PID) controller. The chamber may be vacuumed to a target pressure prior to introducing the test sample. The chamber may be purged with nitrogen prior to intruding the test sample. The target pressure may be approximately 1.4 kPa.

BRIEF DESCRIPTION OF THE FIGURES

FIG. 4a shows the test results from several test runs with pure n-Dodecane test sample masses ranging from 78.2 mg to 496.6 mg;

FIG. 4b is a graph showing the results for the test data from FIG. 4a;

DETAILED DESCRIPTION

Figure 1:
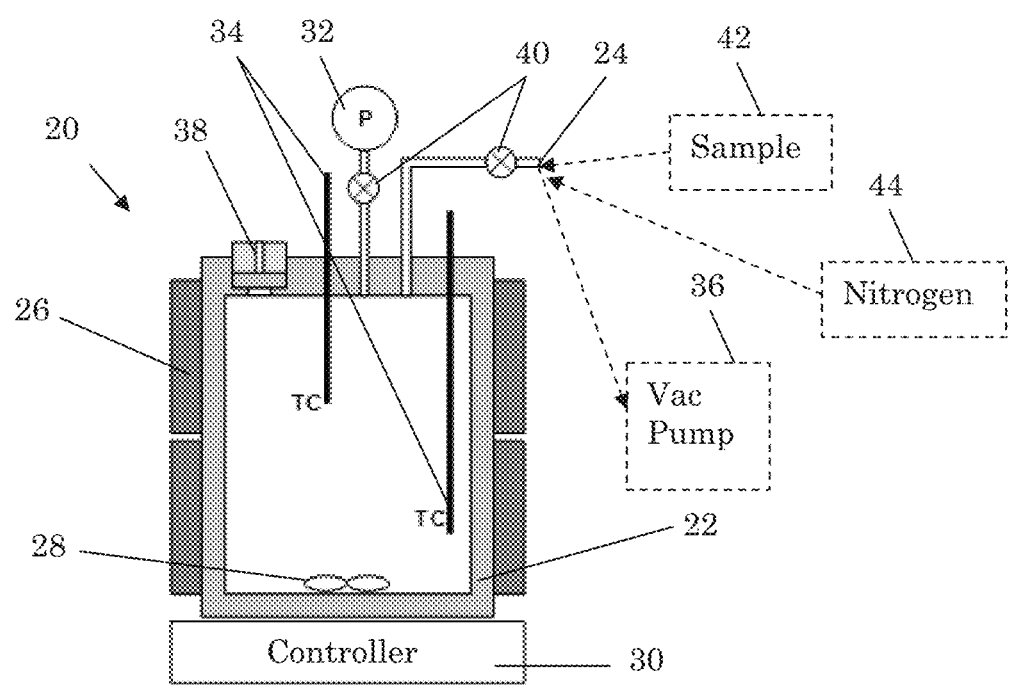
FIG. 1 is a block diagram of a constant-volume based apparatus configured to determination of the mixture average molecular weight of a liquid fuel sample.

Disclosed are two exemplar system configurations and methods for the determination of the mixture average molecular weight of complex mixtures such as transportation fuels. Complex mixtures of this type may include various species and may have varying molecular structure and atomic composition. Such complex mixtures reside entirely in the vapor (gaseous) state for some range of pressures and temperatures, without chemical decomposition or reaction. The techniques disclosed herein are designed for complex mixtures with similar associated distillation curve parameters, including: hydrocarbon/oxygenated hydrocarbon mixtures used in ground transportation, aeropropulsion fuels, and liquid rocket propellants. It is easily envisioned by those knowledgeable in the art that this method can also be applied to other hydrocarbon fluids and gaseous hydrocarbon mixtures.

One aspect of developing a more accurate measurement of average molecular weight for fuels relates to experimental characterization and predictive modeling of their fully pre-vaporized global combustion behavior. See e.g., Dooley, S. Et. al., "A Jet Fuel Surrogate Formulated by Real Fuel Properties" Combust Flame 157:2333-2339 (2010); Dooley, S. Et. al., "The Experimental Evaluation of a Methodology for Surrogate Fuel Formulation to Emulate Gas Phase Combustion Kinetic Phenomena", Combust Flame 159:1444-4466 (2012). Dooley, S. et. al., "The Combustion Kinetics of a Synthetic Paraffinic Jet Aviation Fuel and a Fundamentally Formulated, Experimentally Validated Surrogate Fuel", Combust Flame 159: 3014-3020 (2012). The average molecular weight is one of four combustion property targets. The others are Derived Cetane Number (ASTM D6890), Hydrogen/Carbon (H/C) ratio (ASTM D5291), and Threshold Sooting Index, TSI. For TSI, see e.g., Mensch, A., R. J. Santoro, T. A. Litzinger, S.-Y. Lee, "Sooting Characteristics of Surrogates for Jet Fuels", Combust Flame 157:1097-1105 (2010)), which depends upon the Smoke Point (ASTM D1322). The Smoke Point was used to characterize real fuels in order to determine surrogate mixtures of only a few components that share very similar global combustion properties to those of a real fuel having the same property targets. As a result of the techniques disclosed herein, now all of the four combustion property targets can be determined using simple fundamental experimental procedures that each requires only a small fuel sample and less than one hour.

The average molecular properties of a specific fuel directly impact chemical equilibrium, reaction kinetics, and vapor density calculations. For example, in experimental and modeling studies of real fuels of complex species composition, it is desirable to define the equivalence ratio of a mixture of the specific fuel vapor with an oxidizer and inert. Average molecular weight of a fuel is also important to assess the relative diffusive extinction strain rate associated with the specific fuel. See e.g., Won S. H., S. Dooley, F. L. Dryer, and Y. Ju, "A Radical Index for the Determination of the Chemical Kinetic Contribution to Diffusion Flame Extinction of Large Hydrocarbon Fuels" Combust Flame (2012) 159:541-551. If the chemical elemental composition of the specific fuel is known, the average molecular weight can be used to determine the average molar formula, $C_nH_mO_y$. Experimental methods that require only small fuel sample volumes already exist, e.g. ASTM D5291, for accurately determining the elemental chemical (H—C-0-N) composition of a fuel sample. Another parameter frequently used in assessing relative sooting potential of various fuels is the Threshold Sooting Index (TSI), Mensch et al. (2010). The TSI is determined on the basis of a fuel smoke point (ASTM D1322) and the fuel average molecular weight. The smoke point is a parameter that is reported in the certification of jet fuels.

Presently, the mixture average molecular weight is also required on-highway vehicle engine emission certification (Commission Regulation (EU) No. 582/2011, 2011) with respect to emissions from heavy duty vehicles (Euro VI)). In this procedure, the mixture average molecular weight of the specific fuel is an assumed quantity, based upon historical statistical data. These statistical data vary widely even from petroleum-derived transportation fuels, and are expected to vary significantly more as a result of blending of petroleum derived and alternative fuels. These assumptions induce uncertainties in the calculated emission levels, including those of carbon that are to be expected from the combustion of the specific fuel. (Similar assumptions are made as well in US emission regulations). The emissions thus predicted are the basis for implementing various carbon mitigation methods.

Finally, the average molecular weight is generally important in the characterization of many other composite molecular materials, including polymers, solvents and chemical reagents used for organic synthesis.

One aspect of the method disclosed herein is the use and measurement of fundamental quantities that are technologically established in metrology, coupled to a fundamental scientific theory that is among the most simple and established in the physical sciences. The advantages of this approach include:

1) The use of simple measurands, the technologies for which are well established;
2) Test times of less than five minutes;
3) Accuracies of better than ±1 g/mol;
4) The requirement of only small masses of the analyte;
5) The simple nature of the measurement process and a resulting ability to be readily automated; and
6) No calibration procedure is required, and the results are insensitive to the impurity caused by the residuals from the previous measurements.

A basic principle underlying the measurement of the mixture average molecular weight is the "Ideal Gas Law" of thermodynamics, namely PV=nRT. Where P is the absolute pressure of the gas, V is the volume of the gas, n is the amount of substance of gas (measured in moles), T is the absolute temperature of the gas and R is the ideal, or universal, gas constant. In general the techniques herein may be carried out using a chamber having two fixed conditions and one variable condition selected from three state variables of temperature, pressure and volume. The following example uses a constant volume approach. It should be understood that other approaches may be used without departing from the scope of the disclosure herein, e.g., constant pressure, constant temperature with changes in volume, or constant pressure, constant volume, with changes in temperature.

Utilizing the Ideal Gas Law, it is possible to monitor the change of pressure before and after the injection of a known mass of fuel sample (analyte) into a constant volume chamber:

$$\Delta m = MW \times \Delta PV/RT$$

$$MW = \Delta m RT/\Delta PV$$

Where, m is the mass of substance in grams, MW is the mixture average molecular weight of the sample, T is the chamber temperature in Kelvin, R is the ideal gas constant (8.314 $JK^{-1}$ $mol^{-1}$), V is the volume of chamber in cubic meters, and P is the pressure in Pascals. The same techniques may be used similarly in the other configurations for the three parameters of pressure, temperature and volume, as noted above.

FIG. 1 is a block diagram of an apparatus 20 configured to determination of the mixture average molecular weight of a liquid fuel sample. In this example, the apparatus 20 includes a constant-volume chamber 22 with an inlet/outlet 24. The constant constant-volume chamber 22 generally heated by a heating element 26. A magnetic stirrer 28 may also be provided in order to achieve uniformity of both temperature and mixture within the volume. In this example the heating element 26 is an electrical resistance heater shown in direct contact with the constant-volume chamber 22 but other forms of heating elements, e.g., inductive or convective, may be used without departing from the scope of the disclosure herein. It should be understood that the heating element 26 and magnetic stirrer 28 may have associated controllers as generally shown by reference number 30. It should be understood that controller 30 may include one or more processors configured to automate the disclosed methods.

The apparatus 20 also includes a pressure gauge 32, one or more thermocouples 34, a vacuum pump 36 and a gastight septum 38 configured for syringe injection of the sample under test. It should be understood that pressure gage 32 may be implemented as one or more pressure sensors coupled to a controller 30 to automate the determination of the change in pressure for a given fuel sample under test. In this example, two thermocouples 34 are installed to measure the temperature inside the chamber and are used to control the temperature of the sample inside the constant-volume chamber 22. For example, controller 30 may include a proportional-integral-derivative (PID) controller. A PID controller, as is well known in the art, generally calculates an "error" value as the difference between a measured process variable and a desired setpoint. In this example, the controller 30 minimize the error by adjusting the heating element to achieve a desired temperature setpoint based on the temperature readings from the thermocouples 34. In general, pressure range for the measurements to be performed and the selected temperature setpoint are chosen such that the sample under test will exist entirely in the vapor state, without decomposition or chemical reaction.

The pressure gauge/sensor 32 is generally used to monitor the pressure in the constant-volume chamber 22 before and after the delivery of the analyte. The sample, a known mass of analyte is prepared and introduced into the constant volume. The state of the analyte may be solid, liquid, or gas, so long as the above criteria relating to full vaporization to gaseous state noted above are maintained. For application to liquids, the liquid analyte, is prepared in a gas-tight hypodermic syringe as generally shown by block 42. The mass of analyte sample to be injected may be determined using a variety of methods including gravimetric measurements. The sample is delivered to the constant-volume chamber 22 through the septum 38. One or more valves 40 may be provided to control the flow of fluid during operation of the apparatus 22.

Figure 2:
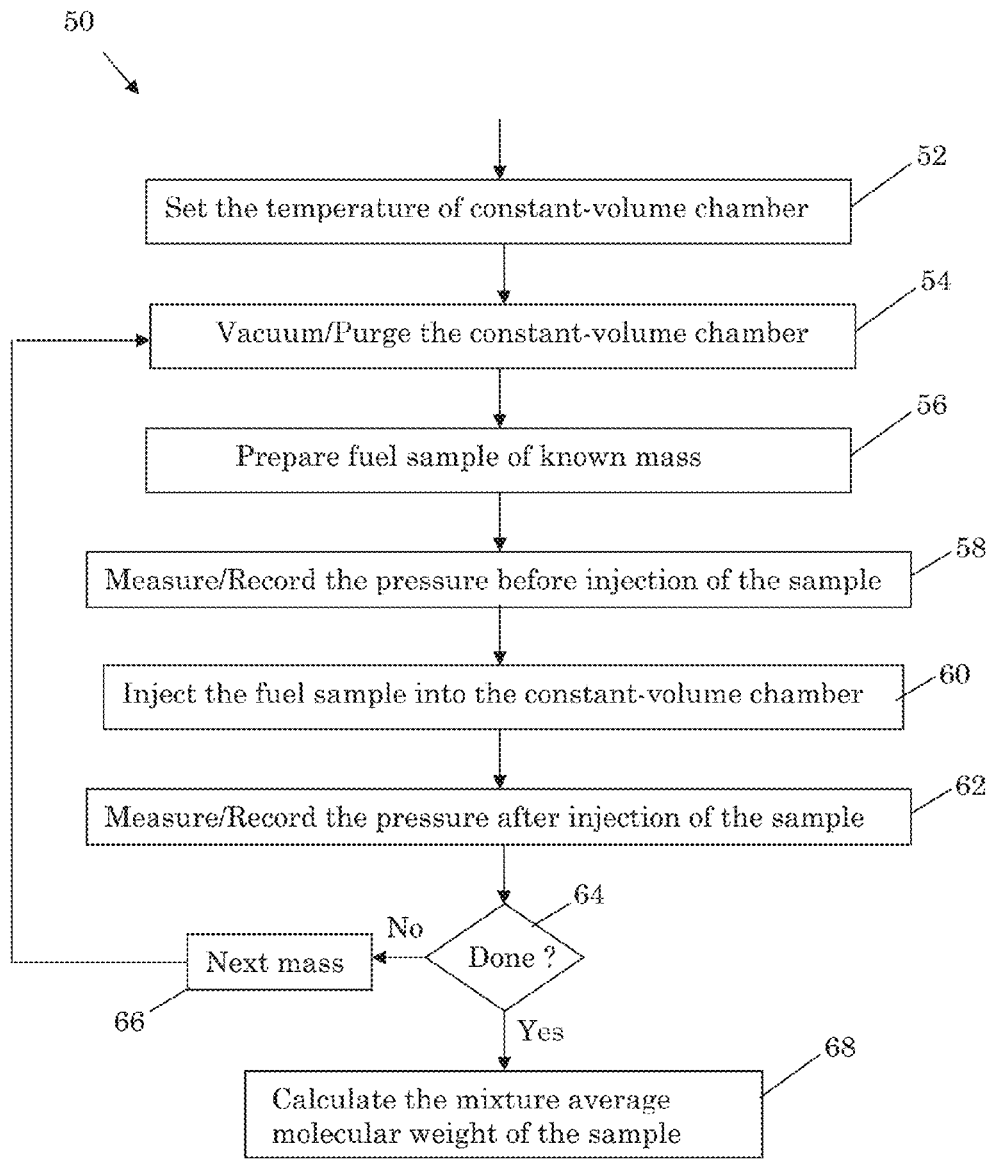
FIG. 2 is a flowchart showing implementation of a constant volume based method for determining the mixture average molecular weight of a liquid fuel sample.

FIG. 2 is a flowchart showing implementation of a method for determining the mixture average molecular weight of a liquid fuel sample. It should be understood that any flowcharts contained herein are illustrative only and that that other entry and exit points may be implemented. It should also be understood that the method may be at least partially computer/microprocessor implemented using one or more processors and associated hardware. Accordingly, time-out functions, error checking routines and the like (not shown) would normally be implemented in typical system hardware/software. It should also be understood that system hardware/software may run continuously after being launched. Accordingly, any beginning and ending points are intended to indicate logical beginning and ending points that can may integrated with other hardware or portions of code and carried out or executed as needed. The order of execution of any of the blocks may also be varied without departing from the scope of this disclosure. Implementation of these aspects in hardware and/or software is readily apparent and well within the grasp of those skilled in the art based on the disclosure herein.

Referring to FIG. 2, using the apparatus 20 disclosed above, a method 50 for determining of the mixture average molecular weight of a liquid fuel sample is as follows.

1) Set the temperature of constant-volume chamber 22 (usually less than 200° C. or 473° K) as generally shown by block 52. The temperature must be high enough that for the pressures to be measured such that the entire sample is assured to exist in the vapor (gaseous) state with no condensed fraction, decomposition, or chemical interactions.

2) Apply a vacuum to the constant-volume chamber 22 using the vacuum pump 36. The target pressure may be approximately 0.2 psi (1.4 kPa) or lower as generally shown by block 54. Prior to vacuuming, the constant-volume chamber 22 may also be purged with nitrogen (44 in FIG. 1), e.g., 2 or 3 times, with the vacuum pump 36. This generally enhances thermal mixing and also helps clean the walls of any absorbed fuel sample materials.

3) Prepare a fuel sample 42 in the syringe and measure the mass as generally shown by block 56. A typical sample may be 100 to 200 mg depending on the fuel. In this example a Mettler Toledo, MS1045/03 scale was used (0.1 mg readability). It should be understood that a wide variety of scales or mass measurement devices or approaches may be used. It should also be understood that the preparation of a plurality of fuel samples, each with a different known mass and the delivery of the sample to the constant-volume chamber 22, may be automated without departing from the scope of the disclosure herein.

4) Measure/record the initial pressure in the constant-volume chamber 22 before injecting the fuel sample as generally shown by block 58. It may also be desirable to close the valve 40 downstream of the pressure gauge (to prevent from damaging the pressure gauge/sensor by possible condensation of fuel sample).

6) Inject the fuel sample in the syringe through the septum 38 as generally shown by block 60.

7) Measure/record the resulting pressure in the constant-volume chamber 22 after injecting the fuel sample as generally shown by block 62. It may be desirable to delay for a period of time to allow for full vaporization of the test sample, e.g., 1 min. If the valve 40 downstream of the pressure gauge was previously closed it will be necessary to the valve 40 to measure the resulting pressure.

8) Repeat the process, e.g., steps 2-7, several times, varying the mass of the fuel samples (typically more than 5 times) as generally shown by blocks 64 and 66. The fixed conditions, i.e., temperature and volume, are held essentially constant during all test runs. In general, the more accurately the fixed conditions are controlled, the more accurate the calculated mixture average molecular weight will be. For example, the following accuracy levels produce suitable results: a two Kelvin uncertainty in temperature control, and a pressure measurement uncertainty of 0.07 kPa yields the molecular weight uncertainties reported in Table 1.

9) Calculate the mixture average molecular weight based on the measured mass and pressure differences as generally shown by block 68. Of major importance to the small uncertainties associated with the described method is the linear relationship of pressure and temperature at constant volume. mixture average molecular weight is the gradient of the linear function describing the measured pressure v. integrated sample mass injected data, as determined by linear regression or other known analysis methods, It should be understood that the controller 30 may include one or more processors configured to 1) perform PID control for temperature and/or 2) perform linear regression to generate line based on the data gathered from the fuel samples (the slope of the line being equal to the molecular weight of the fuel under test).

Figure 3:
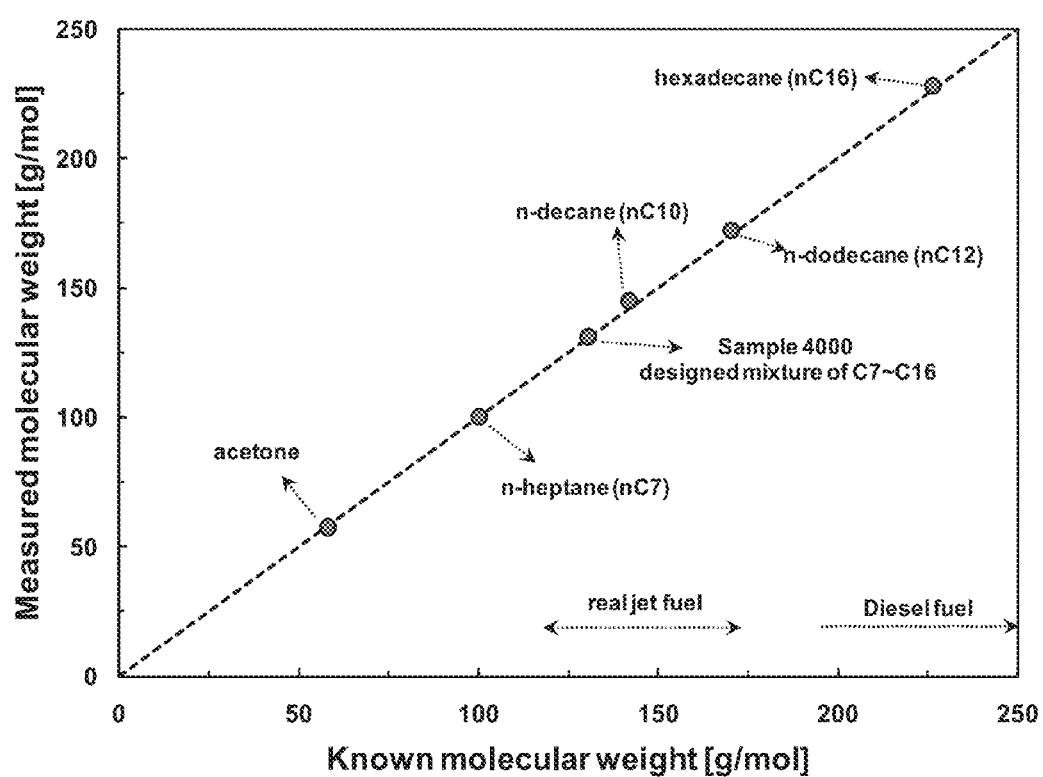
FIG. 3 is a graph displays the measurements of the mixture average molecular weight produced using the method described in FIGS. 1 and 2, compared to the known values of the tested analytes. The analytes include samples of fluids composed of only one known molecular species, as well as defined mixtures of known molecular species.

Following the approach described above, ten test measurements were performed for pure as well as multi component mixtures of varying molecular weight, known composition, thermophysical (vapor pressure) and chemical properties (potential to decompose pyrolytically). FIG. 3 is a graph that displays the measurement of the mixture average molecular weight produced using the above methods, compared to the known values of the tested analytes. As shown in FIG. 3, the process as executed by the prototype device can provide accurate measurement of mixture average molecular weight (less than 5% uncertainty) over the entire range of values typical of gasoline, diesel, and gas turbine fuels derived from petroleum and present alternative feed stocks. Here the accuracy of the measurement is limited only by material and procedural issues specific to the prototype device. It is expected that the resulting uncertainties from these issues can be easily minimized by proper design and operation, in principle providing accuracies of greater than 1 g/mol.

Figure 4B:
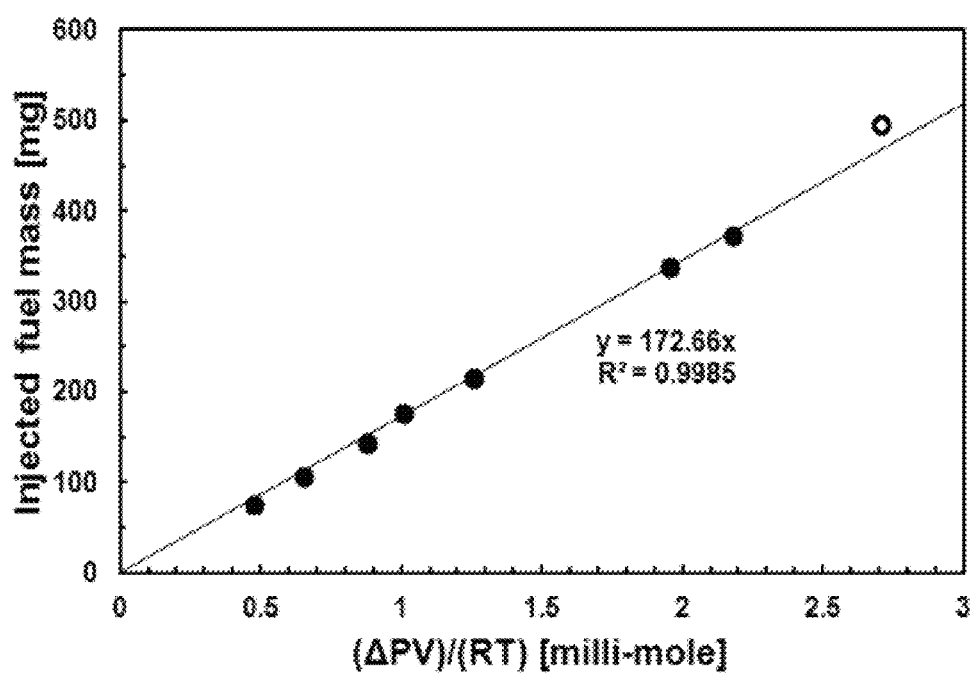

FIG. 4a shows the test results from several test runs with n-Dodecane (170.33 g/mol) with test samples ranging in mass from 78.2 mg to 496.6 mg. Once the data is collected it is correlated to a line having a slope equal to the mixture average molecular weight of the liquid fuel sample. FIG. 4b is a graph showing the results for the test data from FIG. 4a. Overall the system is capable of producing accurate results in less than 30 min per each fuel sample. Less than 1 g of fuel sample required. Results are within ±3 g/mol (max.) uncertainty, mostly less than 2. Finally, Table 1 shows the summary of molecular weights for a number of real gas turbine fuel samples as determined by the method described above.

TABLE 1

| Fuel Samples | MW measured [g/mol] | Uncertainty [g/mol] |
| --- | --- | --- |
| Jet-A POSF 4658 | 157.5 | 2.0 |
| JP-8 POSF 6169 | 153.9 | 1.4 |
| JP-8 POSF 5699 | 153.9 | 2.7 |
| S-8 POSF 4734 | 153.9 | 0.7 |
| SASOL IPK POSF 7629 | 149.2 | 1.0 |
| SHELL SPK POSF 5729 | 136.7 | 1.1 |
| HRJ TALLOW POSF 6308 | 161.0 | 1.4 |
| HRJ CAMELINA POSF 7720 | 165.0 | 0.6 |
| JP-8/SPK 50/50 POSF 7717 | 144.0 | 1.7 |
| JP-8/IPK 50/50 POSF 7718 | 146.1 | 0.8 |
| JP-8/HRJ-T 50/50 POSF 7719 | 155.8 | 0.6 |
| JP-8/HRJ-C 50/50 POSF 7721 | 160.2 | 1.3 |
| GEVO ATJ POSF 10151 | 173.0 | 1.7 |
| JP-8/GEVO ATJ 50/50 Blend POSF10153 | 161.2 | 2.7 |
| Shell Jet A POSF 10325 | 147.6 | 0.9 |
| NuStar Refining LLC JP-8 10264 | 141.4 | 1.1 |
| Valero JP-5 POSF 10289 | 156.1 | 0.8 |
| AARF JP-8 POSF 8296 | 131.7 | 1.3 |
| AARF JP-8 POSF 9405 | 175.2 | 0.9 |
| IPK-UN1223 | 148.5 | 0.8 |
| Nor-Par | 156.4 | 1.2 |
| Iso-Par | 175.7 | 1.9 |
| Aromatic 100 | 116.0 | 1.4 |
| Aromatic 150 | 129.8 | 0.9 |
| Exxol D95 | 176.7 | 1.2 |

Figure 5:
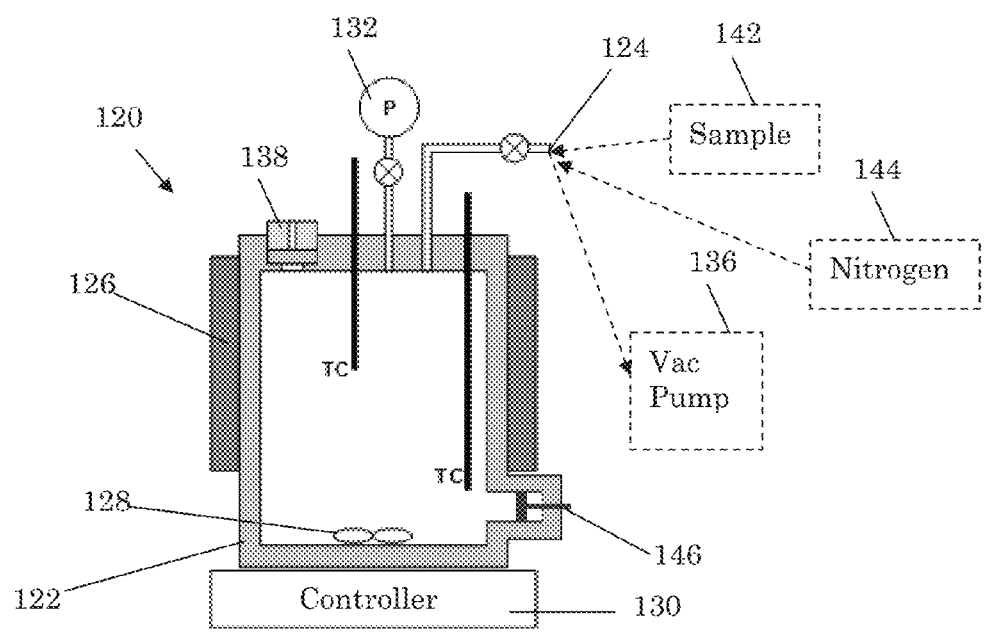
FIG. 5 is a block diagram of a constant pressure apparatus configured to determination of the mixture average molecular weight of a liquid fuel sample.

It is understood by those knowledgeable in the field that many variations of the disclosed system and method are encompassed by the disclosure herein. For example, the system may be implemented in a constant pressure-constant temperature/variable volume or a constant pressure-constant volume/variable temperature configuration. For example FIG. 5 is a block diagram of an apparatus 120 configured to determination of the mixture average molecular weight of a liquid fuel sample based on a constant pressure. The apparatus generally includes similar structure as disclosed in FIG. 1 above. In this example, the apparatus 120 includes a constant-pressure chamber 122 with an inlet/outlet 124. The constant constant-pressure chamber 22 may be heated by a heating element 126. A magnetic stirrer 128 may also be provided in order to achieve a uniformity of both temperature and mixture. The apparatus 120 also includes a pressure gauge 132, one or more thermocouples 134, a vacuum pump 136 and a gastight septum 138 configured for syringe injection of the sample under test. Constant pressure may be achieved via a movable piston 146 or other method to permit variation in the chamber volume. Volume measurements may be accomplished via a variety of methods including correlations between the piston position and the volume of the chamber 122 to achieve constant pressure. It should be understood that movable piston 146 or other volume change method may be configured for manual operation or may be controlled via controller 130 using a PID approach based on a pressure set point and readings from pressure sensors (not shown).

Figure 6:
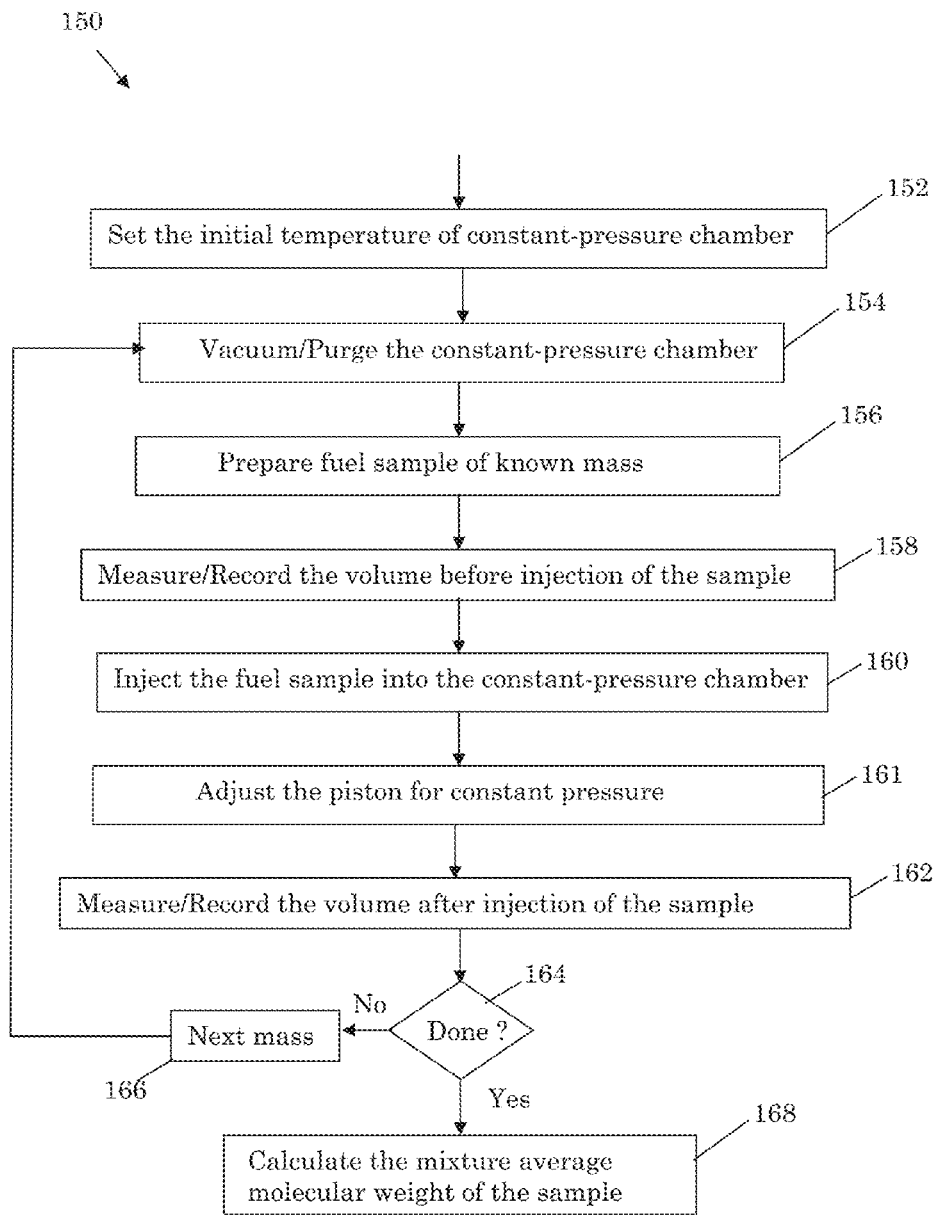
FIG. 6 is a flowchart showing implementation of a constant pressure based method for determining the mixture average molecular weight of a liquid fuel sample.

Referring to FIG. 6, using the apparatus 120 disclosed above, a method 150 for determining of the mixture average molecular weight of a liquid fuel sample is as follows. It should be understood that each time a sample is processed the following applies:

1) Set the temperature of the constant-pressure chamber 122 (usually 200° C. or 473° K) as generally shown by block 52.

2) Apply a vacuum to the constant-pressure chamber 122 using the vacuum pump 136. The target pressure may be approximately 0.2 psi (1.4 kPa) or lower as generally shown by block 154. Prior to vacuuming, the constant-pressure chamber 122 may also be purged with nitrogen (144 in FIG. 5), e.g., 2 or 3 times, with the vacuum pump 136. This generally enhances thermal mixing.

3) Prepare a fuel sample 142 in the syringe and measure the mass as generally shown by block 156. A typical sample may be 100 to 200 mg depending on the fuel. In this example a Mettler Toledo, MS104S/03 scale was used (0.1 mg readability). It should be understood that a wide variety of scales or mass measurement devices or approaches may be used.

4) Measure/record the initial volume in the constant-pressure chamber 122 before injecting the fuel sample as generally shown by block 158.

6) Inject the fuel sample in the syringe through the septum 138 as generally shown by block 160.

7) Adjust the piston (or other volume change device) so that pressure remains constant as generally shown by block 161.

8) Measure/record the resulting volume in the constant-pressure chamber 122 after injecting the fuel sample as generally shown by block 162.

9) Repeat the process, e.g., steps 2-8, several times, varying the mass of the fuel samples (typically more than 5 times) as generally shown by blocks 164 and 166;

10) Calculate the mixture average molecular weight based on the measured mass and volume differences as generally shown by block 168.

It should be understood that the method disclosed above may be carried out in similar fashion using temperature as a variable. The method and instrumentation disclosed herein are very compatible with those pieces of instrumentation presently used for determining the autoignition properties of a fuel, for example the apparatuses used to determine the Derived Cetane Number of distillate fuels. This instrumentation presently uses a repetitive pulsed injection of a fuel spray of known liquid volume into a high pressure, high temperature volume of air to determine the absolute ignition delay of the fuel and air mixture, thus rating the ignitability of the fuel relative to that of a number of fuel reference materials. The methods to produce DCN are used in every refinery to certify a diesel fuel to be fit for use in specific engine types. The approach described here could be integrated into test procedures with these devices or may be carried out separately.

The disclosed method and apparatus can be employed with American Society for Testing and Materials standardized products related to fuel and refinery distillate testing. For example, modifications to the Advanced Engine Technology Ltd. Ignition Quality Testing apparatus will allow for the incorporation of the process described herein. The IQT is already an integral part of many refinery operations worldwide and is fully recognized as a qualified instrument for determining fit for use cetane numbers for diesel fuels (ASTM D-6890-09). International standards based upon its use also exist. In addition, similar instrumentation and procedures (ASTM D7170-6) for determining derived cetane number, a Fuel Ignition Tester (FIT), is produced by Dresser Waukesha. Dresser Waukesha was the original manufacturer of CFR research engines and procedures for determining Octane and Cetane number of gasolines and Diesel fuel. The disclosed method and apparatus can be employed for both applications, though the gasoline application can also be employed as a standalone rather than an integrated instrument design. The disclosed method and apparatus can also be employed with InnoSense LLC instrumentation for an automated method for determining the smoke point of fuels. Combined with the presently disclosed method for measuring molecular weight, one could automate the determination of not only smoke point, but the Threshold Sooting Index.

Although features and elements are described above in particular combinations, each feature or element can be used alone without the other features and elements or in various combinations with or without other features and elements. The methods or flow charts provided herein may be implemented in a computer program, software, or firmware incorporated in a non-transitory computer-readable storage medium for execution by a general purpose computer or a processor. Examples of computer-readable storage mediums include a read only memory (ROM), a random access memory (RAM), a register, cache memory, semiconductor memory devices, magnetic media such as internal hard disks and removable disks, magneto-optical media, and optical media such as CD-ROM disks, and digital versatile disks (DVDs).

What is claimed is:

1. A method for determining the average molecular weight of a complex-mixture from a plurality of test samples of the complex mixture, the method comprising:
   a. providing a chamber having two fixed conditions and one variable condition selected from three state variables of temperature, pressure and volume;
   b. introducing a test sample of known mass into the chamber;
   c. setting operating conditions of the state variables such that the test sample will be fully vaporized into a gaseous state without decomposition or other chemical reaction;
   d. measuring the change of the variable condition after full vaporization of the test sample is achieved;
   e. repeating steps b-d for several test samples having different masses; and
   f. determining the average molecular weight of the complex mixture as a linear gradient of the relationship for the change of variable condition as a function of test sample mass, wherein the complex mixture comprises a plurality of molecular species.

2. The method of claim 1 wherein the fixed conditions are volume and temperature and the variable condition is pressure.

3. The method of claim 1 wherein the fixed conditions are temperature and pressure and the variable condition is volume.

4. The method of claim 1 wherein determining the average molecular weight comprises performing a linear regression on the measured change of variable condition as a function of test sample mass.

5. The method of claim 4 wherein the linear regression generates a line having a slope equal to the average molecular weight of the fuel under test.

6. The method of claim 1 wherein the fixed conditions are held essentially constant across multiple test samples.

7. The method of claim 1 wherein at least one of the fixed conditions is controlled using a proportional-integral-derivative (PID) controller.

8. The method of claim 1 further comprising vacuuming chamber to a target pressure prior to introducing the test sample.

9. The method of claim 1 further comprising purging the chamber with nitrogen prior to intruding the test sample.

10. An apparatus configured to determine of the average molecular weight of a complex mixture from a plurality of test samples, the apparatus comprising:
  a chamber having two fixed conditions and one variable condition selected from three state variables of temperature, pressure and volume;
  at least one sensor configured to measure the variable condition for the plurality of test samples; and
  a controller configured to determine the average molecular weight of the complex mixture as a linear gradient (slope) of the relationship for the change of variable condition as a function of test sample mass,
  wherein the complex mixture comprises a plurality of molecular species.

11. The apparatus of claim 10 wherein the fixed conditions are volume and temperature and the variable condition is pressure.

12. The apparatus of claim 10 wherein the fixed conditions are temperature and pressure and the variable condition is volume.

13. The apparatus of claim 10 wherein average molecular weight is determined by performing a linear regression on the measured mass and change in variable condition associated with the plurality of test samples.

14. The apparatus of claim 13 wherein the linear regression generates a line having a slope equal to the molecular weight of the complex mixture.

15. The apparatus of claim 10 wherein the fixed conditions are held essentially constant across multiple test samples.

16. The apparatus of claim 10 further comprising a proportional-integral-derivative (PID) controller configured to control at least one of the fixed conditions.

17. The apparatus of claim 10 further comprising a vacuum pump configured to vacuum the chamber to a target pressure prior to introducing the test sample.

18. The apparatus of claim 10 further comprising a nitrogen supply configured to purge the chamber with nitrogen prior to introducing the test sample.

* * * * *